May 31, 1949. J. D. BROWNELL Plant Pat. 841
ROSE PLANT
Filed April 22, 1946
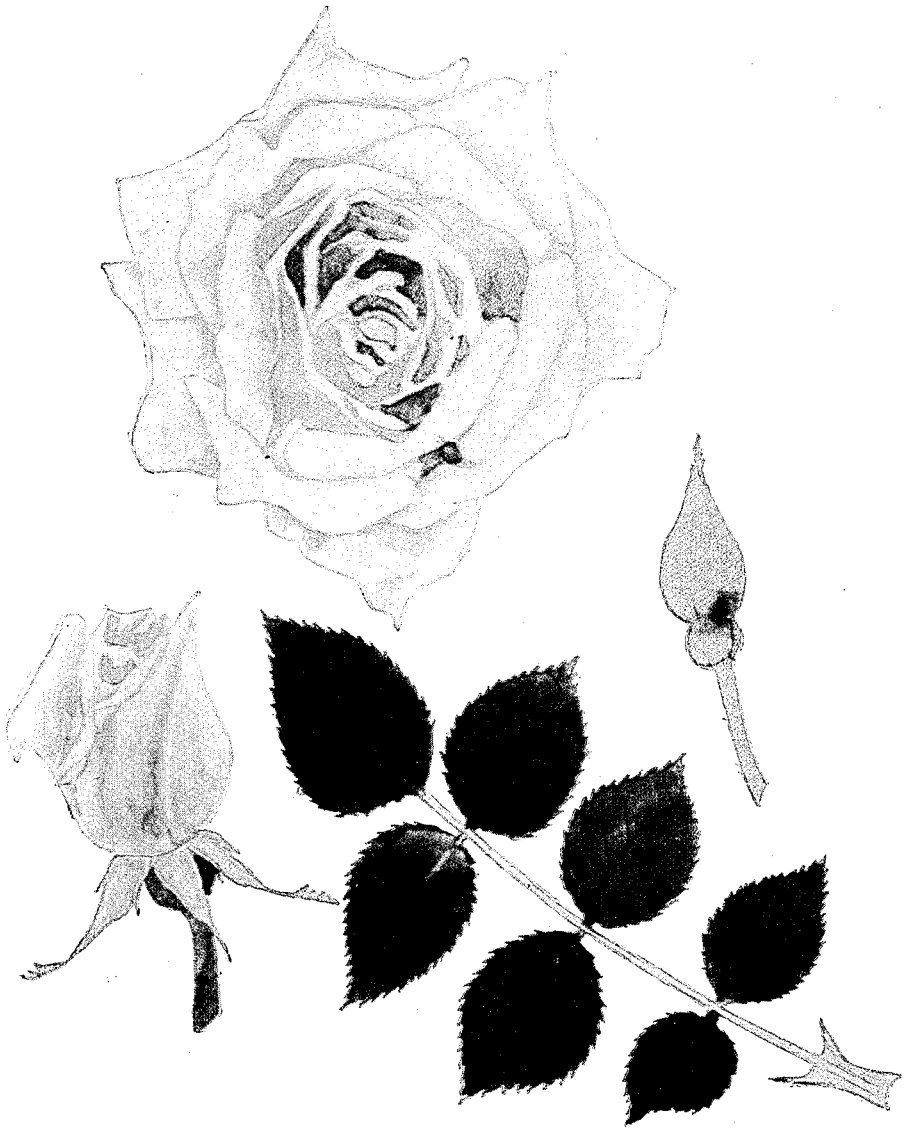
Josephine D. Brownell.
INVENTOR.
BY Patented May 31, 1949

Plant Pat. 841

UNITED STATES PATENT OFFICE

841

ROSE PLANT

Josephine D. Brownell, Little Compton, R. I.

Application April 22, 1946, Serial No. 663,868

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States:

The red to pink shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by black-spot, under certain definite conditions of exposure, without any cultural control.

In the accompanying drawing forming a part of this specification I have shown my new rose in its natural colors, that is, as near as is possible to do so artificially.

My new rose is otherwise described as follows:

*Essential information*

*Type.*—Hybrid tea, *Rosa wichuraiana* hybrid, dwarf to ascending to tall to climber, for garden display, cut flower and forcing or growing under glass.

*Class.*—Hybrid tea crossed with *Rosa wichuraiana*, further restricted by originator to include only those varieties that can survive moderately low sub-zero temperatures.

*Breeding.*—This variety was produced and bred by me and under my direction by propagation and cross pollenation.

It came into being as a seedling grown from a seed borne on a plant of "Pink Princess," Plant Patent Number 459, and the pollen parent of my new rose was "Crimson Glory," Plant Patent Number 105.

The pollenation that fertilized the seed that grew into my new rose, as well as the pollenation that produced its seed parent were directed by me and were performed by emasculating flowers and placing thereon a bag protecting from self and foreign pollen. These bags were later removed and the flowers were hand pollenated with a camel's hair brush and the bags immediately replaced. The date of this pollenation was July 3, 1943.[1] The seed was planted under my direction on December 1, 1943, and the date of the first flower was July 18, 1944.

The plant and flower seemed to me to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1944–5 inclusive and the characters have successively reproduced, true to the original seedling.

*Flower*

*Habit.*—It blooms out of doors in Little Compton, beginning about three days prior to the average beginning time of commercial hybrid teas and continues relative to growth of the plant until frost.

*Flowers borne.*—Often one and frequently two or three and occasionally more on each stem, in the usual hybrid tea type of cluster. The pedicels and peduncles are medium to large in diameter and length, erect, stiff, almost smooth, free from large prickles and bristles but with a few very small prickles varying to small hairs. Stems are long, diameter medium to large and notably stiff and rigid.

*Quantity of bloom.*—Free, being cumulative in quantity from year to year as the plant increases in size, flowering through the summer.

[1] This and other dates herein are approximate.

*Fragrance.*—Distinctive, pleasing China tea in combination with that of *Rosa wichuraiana* and musk, under favorable environment.

*Bud.*—Neck normal to large as described, opens well, being little to not at all affected by hot or wet weather or both, as to color and form, except at very high temperatures the color is less intense and the form of the petals is less recurled.

Before the calyx breaks the size is medium to large, form moderately pointed, frequently with one or more sepals having foliaceous parts extending beyond the apex of the calyx up to about three quarters of an inch, the number and size of the foliaceous parts being variable and frequently having one narrow, pointed, serrate appendage on each side of the sepals, otherwise the sepals are usually normal and regular, tapering to lanceolate at their apex, turning back nearly perpendicular to the pedicel as the bud opens.

Color of the bud as the calyx opens—both sides of petals variable between "Bordeaux"[2] and "Carmine."

*Bloom.*—As the bud opens and the flower develops the color varies, both sides of the petals, slowly changes in degree as affected by sunlight exposure toward Tyrian Rose and Rose Color. The petals have a characteristic brilliance.

The flower is usually 4 to 5½ inches in diameter when fully open, infrequently more or less, petals average around 60, frequently some smaller petals and petaloids in the center, variable in number.

The flower opens high centered, formal, recurled, showing stamens and pistil as petals fall. The petals are variable from obovate to ovate to irregular and frequently with surfaces variously warped and edges especially of the smaller petals frequently notably irregular. Texture is medium to thick and leathery; both sides brilliant; with slight veining which is not prominent. The time of opening in favorable conditions is two to four days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs.*—Stamens variable in quantity, medium and slightly uneven in length.

Anthers, Light Salmon Orange.

Filaments, nearly Mustard Yellow.

Pistils are several of slightly uneven length, averaging around one-half inch long.

Ovaries are usually all inclosed.

Hips frequently develop to ovoid to globular, color comparable with under side of leaves with variable colored overlay on the side exposed to the sun, moderately smooth; walls, thin, fleshy, medium large.

Sepals are persistent and break off easily.

*Plant*

*Foliage.*—Is abundant, of compound leaves of three to five leaflets near the flower, five leaflets lower down the stem and frequently seven leaflets in the middle of the stem and nearer the base. Size of leaflets medium, averaging in size a little larger than half way between the average hybrid tea and the *Rosa wichuraiana* leaflets. As the plants develop in size some of the leaflets develop to twice the size described above. Form of leaflets

[2] Color references hereinafter, unless otherwise noted are to Robert Ridgway Color Standards.

usually ovate with apex moderately acute, base rounded frequently slightly acute. Margins with medium pointed serrations, petiolules short.

Color of leaflets on the upper surface is slightly variable from Dark Dull Yellow Green, with reverse side nearly Asphodel Green frequently overlaid with Dahlia Carmine.

The rachises are medium, moderately narrow to slender, upper side smooth except some very short hairs on edges. Under side moderately smooth, usually 3 to 5 short prickles.

Stipules are medium to long, averaging about three-quarters of an inch long, with sharp points, the upper edges of which normally form an angle of about 85 degrees.

Habit, dwarf, becoming bushy to tall; upright compact, more cumulative in growth from year to year than the normal hybrid tea rose plant, by stems or canes from the base and by rebranching and growth and enlargement and extension of the stems from the base. The growth is moderately free at first, developing more rapidly after one or two years under favorable vegetative opportunity.

Color of mature stems is the same as that of the upper surface of mature leaves, shading variously lighter and also with overlay of Indian Red variable in intensity.

Prickles, several, frequently two to four between leaves, averaging in length about one-quarter inch, shading from Dahlia Carmine to lighter at the base, turning lighter throughout and later to nearly colorless. Hairs few on upper portions of stems. Color of prickles shading to color of stems.

*Winter resistance.*—A notable characteristic of this new rose is its resistance to moderate sub-zero temperatures in combination with its hybrid tea character and its *Rosa wichuraiana* ancestry. This variety with grafted bud and plant entirely exposed above ground to moderate sub-zero temperatures survived and bloomed normally the following season. The word "temperature" herein refers to the Fahrenheit scale.

*Comparisons.*—Probably the best known rose in commerce comparable with the flower of this new variety is the hardy climber "Bess Lovett," which has much the same color tones in combination with very full petalage, while in this new variety the colors are somewhat deeper, and the petals more recurled. In form this new variety is more formal and the fragrance is more spicy.

My new rose variety is distinguished from application 663,870 in that the branches and stems normally grow at an angle of about 45 degrees in relation to the gravitational influence, and application 663,870 discloses them normally growing at an angle of about 5 degrees in relation to the same.

The branches from the stems of my new rose variety start more frequently from lower eyes, progressively smaller as they branch more nearly from the top. The branches from stems of application 663,870 are usually from abnormally near the end of the stems, frequently large long flowering branches stem from the base of the peduncle and from the second and third eyes below, giving an unusually bright appearance to the growth habit, in comparison with a notable spreading habit of my new rose variety.

The blooms of my new rose variety open their center petals usually in a form warped to doubled over an axis from base to tips; and corresponding petals of the other variety open with their petals in nearly smooth concentric circles with edges somewhat recurled.

My new rose variety when established frequently grows a stem approximately two and one-half feet long with the terminal flower over 5 inches in diameter and with 6 to ten surrounding flowers progressively smaller outward and downward in the clusters, with notably long secondary branches.

The other variety grows its strongest stems very much shorter than my new rose variety and more frequently with one to three blooms to each stem.

Under the midsummer sun my new rose holds its normal color somewhat longer than the other, changing slowly to a lighter shade of the same color, the other changes slowly toward maroon (ordinary dictionary definition).

My new rose is different in form in that, its petals open somewhat more folded on a central axis from the base to the tip, and open wider, thereby averaging under the same conditions, somewhat larger flowers.

Due to the difference in growth habit application 663,870 late in the season will have developed under the same conditions some stems 6 to 10 inches longer.

The fragrance of my new rose more closely resembles that of the China tea in combination of that of *wichuraiana,* the fragrance of the other more nearly resembles that of the Damask rose.

My new rose is distinguished from 663,871 in that it has very many more petals, is very much darker in color, its petals are more bent or folded over an axis from base to tip, the fragrance is of China tea crossed with that of *Rosa wichuraiana,* as distinguished from that resembling the carnation; its petals when fully open more completely cover the center of the flower the center of the other being usually fully exposed.

I claim:

The rose plant variety substantially as shown and described, characterized by its resistance to winter injury, its intensity and continuity of florescence, its long keeping character of the color of its petals and the form of its petals and the form of the flower, variable within certain definite limits, its color as described all in association with its habit of branching from bloom stems and from the base and blooming in hybrid tea manner, and its degree of freedom from premature defoliation by black-spot during the growing season.

JOSEPHINE D. BROWNELL.

No references cited.